US012704511B2

(12) United States Patent
Filali-Ansary et al.

(10) Patent No.: US 12,704,511 B2
(45) Date of Patent: Aug. 11, 2026

(54) METHODS FOR VERIFICATION OF DRUG LEVELS USING DRIED BLOOD SAMPLES

(71) Applicant: Sanofi, Paris (FR)

(72) Inventors: Aziz Filali-Ansary, Paris (FR); Patricia Zane, Bridgewater, NJ (US)

(73) Assignee: Sanofi, Paris (FR)

( * ) Notice: Subject to any disclaimer, the term of this patent is extended or adjusted under 35 U.S.C. 154(b) by 727 days.

(21) Appl. No.: 17/924,064

(22) PCT Filed: May 18, 2021

(86) PCT No.: PCT/EP2021/063107
§ 371 (c)(1),
(2) Date: Nov. 8, 2022

(87) PCT Pub. No.: WO2021/233894
PCT Pub. Date: Nov. 25, 2021

(65) Prior Publication Data

US 2023/0176050 A1 Jun. 8, 2023

(30) Foreign Application Priority Data

May 19, 2020 (EP) .................................... 20315245

(51) Int. Cl.

| | |
|---|---|
| ***G01N 33/564*** | (2006.01) |
| ***G01N 33/49*** | (2006.01) |
| ***G01N 33/68*** | (2006.01) |

(52) U.S. Cl.
CPC ......... *G01N 33/564* (2013.01); *G01N 33/492* (2013.01); *G01N 33/6848* (2013.01)

(58) Field of Classification Search
CPC . G01N 33/564; G01N 33/492; G01N 33/3848
See application file for complete search history.

(56) References Cited

U.S. PATENT DOCUMENTS

| | | | |
|---|---|---|---|
| 2012/0058009 | A1 | 3/2012 | Nogami et al. |
| 2012/0171151 | A1 | 7/2012 | Thomassian |
| 2013/0040857 | A1 | 2/2013 | Anderson |
| 2018/0269047 | A1 | 9/2018 | Zhu |

FOREIGN PATENT DOCUMENTS

| | | | |
|---|---|---|---|
| EP | 2186879 | | 11/2016 |
| JP | 2006-105699 | A | 4/2006 |
| JP | 2018-534554 | A | 11/2018 |
| JP | 2020-502544 | A | 1/2020 |
| JP | 2023-529808 | A | 7/2023 |
| WO | WO 2018/118630 | A1 | 6/2018 |
| WO | WO 2018/189911 | A1 | 10/2018 |
| WO | WO 2021/233860 | A1 | 11/2021 |
| WO | WO 2021/233894 | | 11/2021 |

OTHER PUBLICATIONS

Adaway et al., "Therapeutic drug monitoring and LC-MS/MS," Journal of Chromatography B, Feb. 1, 2012, 883-884:33-49.
Bar-Or et al., "Teriflunomide and its mechanism of action in multiple sclerosis," Drugs, Apr. 2014, 74(6):659-674.
Blix et al., "Drugs with narrow therapeutic index as indicators in the risk management of hospitalised patients," Pharmacy Practice, Jan.-Mar. 2010, 8(1):50-55.
Campbell et al., "Chapter 8: Therapeutic Drug Monitoring in Pregnancy," Clinical Challenges in Theraputic Drug Monitoring, Clark & Dasgupta (eds.), 2016, pp. 185-211.
Efendi, "Clinically Isolated Syndromes: Clinical Characteristics, Differential Diagnosis, and Management," Noro Psikiyatr Ars., 2015, 52(suppl 1):S1-S11.
Filali-Ansary et al., "Dried Blood Spot Methodology in Combination With Liquid Chromatography/Tandem Mass Spectrometry Facilitates the Monitoring of Teriflunomide," Ther. Drug Monit., Aug. 2016, 38(4):471-482.
Genzyme Corporation, "Aubagio: Highlights of prescribing information," Sep. 1, 2012, retrieved on Apr. 26, 2013, retrieved from URL <https://products.sanofi.us/aubagio/aubagio.pdf>, 8 pages.
International Preliminary Report on Patentability in International Appln. No. PCT/EP2021/063107, mailed on Dec. 1, 2022, 12 pages.
International Search Report and Written Opinion in International Appln. No. PCT/EP2021/063107, mailed on Nov. 29, 2021, 16 pages.
Johnson-Davis et al., "Therapeutic Drug Monitoring in Pregnant Patients," Focus Series: Therapeutic Drug Monitoring During Pregnancy and Lactation, Apr. 2020, 42(2):172-180.
Kieseier et al., "Pregnancy outcomes following maternal and paternal exposure to teriflunomide during treatment for relapsing-remitting multiple sclerosis," Neurol. Ther., Dec. 2014, 3(2):133-138.
Lugaresi et al., "Risk-benefit considerations in the treatment of relapsing-remitting multiple sclerosis," Neuropsychiatric Disease and Treatment, 2013, 9:893-914.
Milosheska et al., "Dried blood spots for monitoring and individualization of antiepileptic drug treatment," European Journal of Pharmaceutical Sciences, Apr. 17, 2015, 75:25-39.
Ontaneda et al., "Progressive multiple sclerosis," Curr. Opin. Neurol., Jun. 2015, 28(3):237-243.
Palmer, "Efficacy and Safety of Teriflunomide," Journal of Symptoms and Signs, Dec. 2013, 2(6):444-457.

(Continued)

*Primary Examiner* — Robert A Zeman
(74) *Attorney, Agent, or Firm* — Fish & Richardson P.C.

(57) ABSTRACT

Provided herein are methods for monitoring treatment for multiple sclerosis in a pregnant subject, and determining the efficacy of a treatment for multiple sclerosis in a pregnant subject. These methods include (a) extracting a drug from a dried blood spot (DBS) sample from a pregnant subject after a treatment for multiple sclerosis has been administered to the pregnant subject; (b) performing mass spectrometry on the extracted DBS sample; (c) determining a peak area ratio of the extracted DBS sample to an internal standard; and (d) identifying the administered treatment as being below the internal standard threshold if the plasma concentration of the treatment is less than 1 as compared to the internal standard ratio. Also provided herein are dried blood spot cards, and kits that include a dried blood spot card pre-treated with at least one internal standard.

17 Claims, 3 Drawing Sheets

(56) References Cited

OTHER PUBLICATIONS

Pardo et al., "The sequence of Disease-modifying therapies in relapsing multiple sclerosis: safety and immunologic considerations," Journal of Neurology, Dec. 1, 2017, pp. 2351-2374.
Rezonja Kukec et al., "A simple dried blood spot method for clinical pharamological analyses of etoposide in cancer patients using liquid chromatography and fluorescence detection," Clinica Chimica Acta, Jan. 15, 2016, 452:99-105.
Manicke et al., "Quantitative analysis of therapeutic drugs in dried blood spot samples by paper spray mass spectrometry: an avenue to therapeutic drug monitoring," Journal of the American Society for Mass Spectrometry, Jun. 2011, 22(9):1501-1507.
Mommers et al., "Quantitative analysis of morphine in dried blood spots by using morphine-d3 pre-impregnated dried blood spot cards," Analytica Chimica Acta, Apr. 2013, 774:26-32.

METHODS FOR VERIFICATION OF DRUG LEVELS USING DRIED BLOOD SAMPLES

CROSS REFERENCE TO RELATED APPLICATIONS

The present application is the national stage entry of International Patent Application No. PCT/EP2021/063107, filed on May 18, 2021, and claims priority to Application No. EP 20315245.9, filed on May 19, 2020, the disclosures of which are incorporated herein by reference.

Described herein are methods and kits for analyzing pharmaceutical molecules, such as teriflunomide, in dried blood samples.

Pregnancy brings many uncertainties to the pregnant subject, as well as to the medical care staff that are treating the pregnant subject for various pre-existing medical conditions (e.g., multiple sclerosis, diabetes, hypertension, cancer) and conditions that may have arisen during pregnancy (e.g., gestational diabetes, anemia, hyperemesis gravidarum). It can be beneficial for pregnant subjects and those that are planning a pregnancy to make sure they are receiving the correct doses of medications, and that their drug plasma concentrations remain within a certain acceptable drug plasma concentration range in order to minimize and prevent harm to the unborn fetus(es) and to the pregnant subject.

The present disclosure is based, at least in part, on the discovery that a drop of blood deposited onto a pre-treated filter paper with a determined quantity of stable-labeled $[^{13}C_2,^2H_3]$-teriflunomide (internal standard, ISTD) can be used to accurately and precisely monitor plasma concentration levels of teriflunomide in a subject (e.g., a pregnant subject). The pretreatment of filter paper with ISTD is repeatable and reproducible. The dried blood spot (DBS) sample can be sent to any facility (e.g., a laboratory) equipped with a high performance liquid chromatography mass spectrometer (LC-MS/MS) for determination of teriflunomide level without the need to use a validated method. The methods described herein allow for quick, reliable, reproducible, precise, and non-invasive (e.g., finger prick) monitoring of plasma teriflunomide concentration.

Blood spotting onto the pre-treated filter paper has been found to have no significant effect on the homogeneity of ISTD dispersion or on the accuracy and precision of the method. Extreme hematocrit values of spotted blood (e.g., 25% and 65% hematocrit value in whole blood) have also been found to have no significant effect on the quantification of teriflunomide using pre-treated filter paper.

Provided herein are methods of monitoring treatment for multiple sclerosis in a pregnant subject that include: (a) extracting a drug from a dried blood spot (DBS) sample, the DBS sample being from a pregnant subject after a treatment for multiple sclerosis to the pregnant subject has been administered; (b) performing mass spectrometry on the extracted DBS sample; (c) determining a peak area ratio of the drug in the extracted DBS sample to an internal standard; and (d) identifying the administered treatment as being below an internal standard threshold when the peak area ratio of the drug in the extracted DBS sample to the internal standard is less than 1.

Also provided herein are methods of determining the efficacy of treatment for multiple sclerosis in a pregnant subject that include: (a) extracting a drug from a dried blood sample, the dried blood sample being from a pregnant subject after a treatment for multiple sclerosis to the pregnant subject has been administered; (b) performing mass spectrometry on the extracted DBS sample; (c) determining a peak area ratio of the drug in the extracted DBS sample to an internal standard; and (d) identifying the administered treatment as being effective when the peak area ratio of the drug in the extracted DBS sample to the internal standard is less than 1. Also provided herein are methods of analyzing a blood sample from a dried blood spot that include: (a) extracting a drug from a dried blood sample, the dried blood sample being from a pregnant subject after a treatment for multiple sclerosis to the pregnant subject has been administered; (b) performing mass spectrometry on the extracted DBS sample; (c) determining a peak area ratio of the drug in the extracted DBS sample to an internal standard; and (d) identifying the administered treatment as being below an internal standard threshold when the peak area ratio of the drug in the extracted DBS sample to the internal standard is less than 1.

In some embodiments of any of the methods described herein, the administered treatment is administration of a drug for relapse-remitting multiple sclerosis.

In some embodiments of any of the methods described herein, the administered treatment and the drug are teriflunomide.

In some embodiments of any of the methods described herein, the method further includes after (d): (e) administering an additional dose of teriflunomide to the pregnant subject.

In some embodiments, the additional dose of teriflunomide is between about 7 mg and about 14 mg of teriflunomide.

In some embodiments of any of the methods described herein, the peak area ratio being less than 1 indicates that a level of teriflunomide in the pregnant subject is non-toxic to a fetus of the pregnant subject.

In some embodiments of any of the methods described herein, the method further comprises identifying the administered treatment as being above the internal standard threshold when the peak area ratio of the drug in the extracted DBS sample to the internal standard is greater than 1.

In some embodiments of any of the methods described herein, the method further includes not administering an additional dose of teriflunomide to the pregnant subject.

In some embodiments, the peak area ratio being greater than 1 indicates that a level of teriflunomide in the pregnant subject is harmful to a fetus of the pregnant subject.

In some embodiments of any of the methods described herein, the internal standard threshold is 0.02 mcg/mL of a teriflunomide.

In some embodiments, the teriflunomide is $[^2H_6]$-Teriflunomide or $[^{13}C_2, 2H_3]$-Teriflunomide. In some embodiments, the teriflunomide is $[^2H_6]$-Teriflunomide. In some embodiments, the teriflunomide is $[^{13}C_2, ^2H_3]$-Teriflunomide.

Also provided herein are methods of monitoring treatment for any disease in a pregnant subject that include: (a) extracting a drug from a dried blood spot (DBS) sample, the DBS sample being from a pregnant subject after a treatment for a disease to the pregnant subject has been administered; (b) performing mass spectrometry on the extracted DBS sample; (c) determining a peak area ratio of the drug in the extracted DBS sample to an internal standard; and (d) identifying the administered treatment as being below an internal standard threshold when the peak area ratio of the drug in the extracted DBS sample to the internal standard is less than 1.

Also provided herein are methods of determining the efficacy of treatment for a disease in a pregnant subject that include: (a) extracting a drug from a dried blood sample, the dried blood sample being from a pregnant subject after a treatment for a disease has been administered; (b) performing mass spectrometry on the extracted DBS sample; (c) determining a peak area ratio of the drug in the extracted DBS sample to an internal standard; and (d) identifying the administered treatment as being effective when the peak area ratio of the drug in the extracted DBS sample to the internal standard is less than 1.

Also provided herein are methods of analyzing a blood sample from a dried blood spot that include: (a) extracting a drug from a dried blood sample, the dried blood sample being from a pregnant subject after a treatment for a disease has been administered; (b) performing mass spectrometry on the extracted DBS sample; (c) determining a peak area ratio of the drug in the extracted DBS sample to an internal standard; and (d) identifying the administered treatment as being below an internal standard threshold when the peak area ratio of the drug in the extracted DBS sample to the internal standard is less than 1.

In some embodiments of any of the methods described herein, the administered treatment is administration of a cardiac drug, an anticoagulant, a bronchodilator, an antibiotic, an anti-epileptic, an antidepressant, an antimanic agent, an antipsychotic, an antiretroviral, or an immune modulator.

In some embodiments of any of the methods described herein, the method further includes after (d): (e) administering an additional dose of the drug to the pregnant subject.

In some embodiments of any of the methods described herein, the peak area ratio being less than 1 indicates that a level of the drug in the pregnant subject is non-toxic to a fetus of the pregnant subject.

In some embodiments of any of the methods described herein, the method further comprises identifying the administered treatment as being above the internal standard threshold when the peak area ratio of the drug in the extracted DBS sample to the internal standard is greater than 1.

In some embodiments of any of the methods described herein, the method further includes not administering an additional dose of the drug to the pregnant subject.

In some embodiments, the peak area ratio being greater than 1 indicates that a level of the drug in the pregnant subject is harmful to a fetus of the pregnant subject.

Also provided herein are methods of monitoring treatment for any disease in a subject that include: (a) extracting a drug from a dried blood spot (DBS) sample, the DBS sample being from a subject after a treatment for a disease to the subject has been administered; (b) performing mass spectrometry on the extracted DBS sample; (c) determining a peak area ratio of the drug in the extracted DBS sample to an internal standard; and (d) identifying the administered treatment as being below an internal standard threshold when the peak area ratio of the drug in the extracted DBS sample to the internal standard is less than 1.

Also provided herein are methods of determining the efficacy of treatment for a disease in a subject that include: (a) extracting a drug from a dried blood sample, the dried blood sample being from a subject after a treatment for a disease has been administered; (b) performing mass spectrometry on the extracted DBS sample; (c) determining a peak area ratio of the drug in the extracted DBS sample to an internal standard; and (d) identifying the administered treatment as being effective when the peak area ratio of the drug in the extracted DBS sample to the internal standard is less than 1.

Also provided herein are methods of analyzing a blood sample from a dried blood spot that include: (a) extracting a drug from a dried blood sample, the dried blood sample being from a subject after a treatment for a disease has been administered; (b) performing mass spectrometry on the extracted DBS sample; (c) determining a peak area ratio of the drug in the extracted DBS sample to an internal standard; and (d) identifying the administered treatment as being below an internal standard threshold when the peak area ratio of the drug in the extracted DBS sample to the internal standard is less than 1.

In some embodiments of any of the methods described herein, the administered treatment is administration of a cardiac drug, an anticoagulant, a bronchodilator, an antibiotic, an anti-epileptic, an antidepressant, an antimanic agent, an antipsychotic, an antiretroviral, or an immune modulator.

In some embodiments of any of the methods described herein, the method further includes after (d): (e) administering an additional dose of the drug to the subject.

In some embodiments of any of the methods described herein, the peak area ratio being less than 1 indicates that a level of the drug in the subject is non-toxic to the subject.

In some embodiments of any of the methods described herein, the method further comprises identifying the administered treatment as being above the internal standard threshold when the peak area ratio of the drug in the extracted DBS sample to the internal standard is greater than 1.

In some embodiments of any of the methods described herein, the method further includes not administering an additional dose of the drug to the subject.

In some embodiments, the peak area ratio being greater than 1 indicates that a level of the drug in the subject is harmful to the subject.

In some embodiments of any of the methods described herein, the dried blood sample is a blood sample obtained from a finger prick.

In some embodiments of any of the methods described herein, the dried blood sample is a blood sample obtained from a venipuncture.

In some embodiments of any of the methods described herein, the dried blood sample is a blood sample obtained from an arm prick, a calf prick, a thigh prick, or a palm of hand prick.

In some embodiments of any of the methods described herein, the dried blood sample is stored for a period of time before step (a).

In some embodiments, the period of time is between 12 hours and 14 days.

In some embodiments of any of the methods described herein, the dried blood sample is stored at room temperature.

Provided herein are methods of monitoring treatment for multiple sclerosis in a pregnant subject that include: (a) extracting a drug from a dried blood spot (DBS) sample, the DBS sample being from a pregnant subject after a treatment for multiple sclerosis to the pregnant subject has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) determining that an amount of the drug in the pregnant subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are methods of determining efficacy of treatment for multiple sclerosis in a pregnant subject that include: (a) extracting a drug from a dried blood sample, the dried blood sample being from a pregnant subject after a treatment for multiple sclerosis to the pregnant subject has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

In some embodiments of any of the methods described herein, the administered treatment is administration of a drug for relapse-remitting multiple sclerosis.

In some embodiments of any of the methods described herein, the administered treatment is identified as being ineffective when the peak area ratio of the drug in the extracted DBS sample to the first internal standard and the peak area ratio of the drug in the extracted DBS sample to the second internal standard are less than 1 or when the peak area ratio of the drug in the extracted DBS sample to the second internal standard is greater than 1.

In some embodiments of any of the methods described herein, the peak ratio of the drug in the extracted DBS sample to the first internal standard being less than 1 indicates that a level of the drug in the pregnant subject is non-toxic to a fetus of the pregnant subject.

In some embodiments of any of the methods described herein, the method further comprises identifying the administered treatment as being above a second internal standard threshold when the peak area ratio of the drug in the extracted DBS sample to the second internal standard is greater than 1.

In some embodiments of any of the methods described herein, the method further include not administering an additional dose of the drug to the pregnant subject.

In some embodiments of any of the methods described herein, the peak ratio of the drug in the extracted DBS sample to the second internal standard being greater than 1 indicates that a level of the drug in the pregnant subject is harmful to a fetus of the pregnant subject.

In some embodiments of any of the methods described herein, the first internal standard threshold is a minimum effective concentration of the drug.

In some embodiments of any of the methods described herein, the second internal standard threshold is a minimum toxic concentration of the drug.

In some embodiments of any of the methods described herein, the method further includes after (e): (f) administering an additional dose of the drug to the pregnant subject.

Also provided herein are methods of monitoring treatment for a disease in a pregnant subject that include: (a) extracting a drug from a dried blood spot (DBS) sample, the DBS sample being from a pregnant subject after a treatment for a disease has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) determining that an amount of the drug in the pregnant subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are methods of determining efficacy of treatment for a disease in a pregnant subject that include: (a) extracting a drug from a dried blood sample, the dried blood sample being from a pregnant subject after a treatment for a disease has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

In some embodiments of any of the methods described herein, the administered treatment is administration of a cardiac drug, an anticoagulant, a bronchodilator, an antibiotic, an anti-epileptic, an antidepressant, an antimanic agent, an antipsychotic, an antiretroviral, or an immune modulator.

In some embodiments of any of the methods described herein, the administered treatment is identified as being ineffective when the peak area ratio of the drug in the extracted DBS sample to the first internal standard and the peak area ratio of the drug in the extracted DBS sample to the second internal standard are less than 1 or when the peak area ratio of the drug in the extracted DBS sample to the second internal standard is greater than 1.

In some embodiments of any of the methods described herein, the peak ratio of the drug in the extracted DBS sample to the first internal standard being less than 1 indicates that a level of the drug in the pregnant subject is non-toxic to a fetus of the pregnant subject.

In some embodiments of any of the methods described herein, the method further comprises identifying the administered treatment as being above a second internal standard threshold when the peak area ratio of the drug in the extracted DBS sample to the second internal standard is greater than 1.

In some embodiments of any of the methods described herein, the method further include not administering an additional dose of the drug to the pregnant subject.

In some embodiments of any of the methods described herein, the peak ratio of the drug in the extracted DBS sample to the second internal standard being greater than 1 indicates that a level of the drug in the pregnant subject is harmful to a fetus of the pregnant subject.

In some embodiments of any of the methods described herein, the first internal standard threshold is a minimum effective concentration of the drug.

In some embodiments of any of the methods described herein, the second internal standard threshold is a minimum toxic concentration of the drug.

In some embodiments of any of the methods described herein, the method further includes after (e): (f) administering an additional dose of the drug to the pregnant subject.

Also provided herein are methods of monitoring treatment for a disease in a subject that include: (a) extracting a drug from a dried blood spot (DBS) sample, the DBS sample being from a subject after a treatment for a disease has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) determining that an amount of the drug in the subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are methods of determining efficacy of treatment for a disease in a subject that include: (a) extracting a drug from a dried blood sample, the dried blood sample being from a subject after a treatment for a disease has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

In some embodiments of any of the methods described herein, the administered treatment is administration of a cardiac drug, an anticoagulant, a bronchodilator, an antibiotic, an anti-epileptic, an antidepressant, an antimanic agent, an antipsychotic, an antiretroviral, or an immune modulator.

In some embodiments of any of the methods described herein, the administered treatment is identified as being ineffective when the peak area ratio of the drug in the extracted DBS sample to the first internal standard and the peak area ratio of the drug in the extracted DBS sample to the second internal standard are less than 1 or when the peak area ratio of the drug in the extracted DBS sample to the second internal standard is greater than 1.

In some embodiments of any of the methods described herein, the peak ratio of the drug in the extracted DBS sample to the first internal standard being less than 1 indicates that a level of the drug in the subject is non-toxic to the subject.

In some embodiments of any of the methods described herein, the method further comprises identifying the administered treatment as being above a second internal standard threshold when the peak area ratio of the drug in the extracted DBS sample to the second internal standard is greater than 1.

In some embodiments of any of the methods described herein, the method further include not administering an additional dose of the drug to the subject.

In some embodiments of any of the methods described herein, the peak ratio of the drug in the extracted DBS sample to the second internal standard being greater than 1 indicates that a level of the drug in the subject is harmful to the subject.

In some embodiments of any of the methods described herein, the first internal standard threshold is a minimum effective concentration of the drug.

In some embodiments of any of the methods described herein, the second internal standard threshold is a minimum toxic concentration of the drug.

In some embodiments of any of the methods described herein, the method further includes after (e): (f) administering an additional dose of the drug to the subject. In some embodiments of any of the methods described herein, the dried blood sample is a blood sample obtained from a finger prick.

In some embodiments of any of the methods described herein, the dried blood sample is a blood sample obtained from a venipuncture.

In some embodiments of any of the methods described herein, the dried blood sample is a blood sample obtained from an arm prick, a calf prick, a thigh prick, or a palm of hand prick.

In some embodiments of any of the methods described herein, the dried blood sample was stored for a period of time before step (a).

In some embodiments, the period of time is between 12 hours and 14 days.

Provided herein are systems that include: a mass spectrometry device configured to (i) generate a peak representing a drug in an extracted DBS sample from a pregnant subject after a treatment for multiple sclerosis to the pregnant subject has been administered and (ii) generate a peak representing an internal standard; a computer-readable memory comprising computer-executable instructions; and one or more processors communicatively coupled to the mass spectrometry device and configured to execute the computer-executable instructions, wherein when the one or more processors are executing the computer-executable instructions, the one or more processors are configured to carry out operations comprising: determining a peak area ratio of the drug in the extracted DBS sample to the internal standard; and identifying the administered treatment as being below an internal standard threshold when the peak area ratio of the drug in the extracted DBS sample to the internal standard is less than 1.

Provided herein are systems that include: a mass spectrometer configured to (i) generate a peak representing a drug in an extracted DBS sample from a pregnant subject after a treatment for multiple sclerosis to the pregnant subject has been administered and (ii) generate a peak representing an internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the internal standard; and identifying the administered treatment as being effective when the peak area ratio of the drug in the extracted DBS sample to the internal standard is less than 1.

In some embodiments of any of the systems described herein, the administered treatment and the drug are teriflunomide.

In some embodiments, the peak area ratio being less than 1 indicates that a level of teriflunomide in the pregnant subject is non-toxic to a fetus of the pregnant subject.

In some embodiments, the peak area ratio being greater than 1 indicates that a level of teriflunomide in the pregnant subject is harmful to a fetus of the pregnant subject.

In some embodiments of any of the systems described herein, the internal standard is 0.02 mcg/mL of a teriflunomide. In some embodiments, the teriflunomide is [$^{2}H_6$]-Teriflunomide or [$^{13}C_2$, $^{2}H_3$]-Teriflunomide. In some embodiments, the teriflunomide is [$^{2}H_6$]-Teriflunomide. In some embodiments, the teriflunomide is [$^{13}C_2$, $^{2}H_3$]-Teriflunomide.

Also provided herein are systems that include: a mass spectrometry device configured to (i) generate a peak representing a drug in an extracted DBS sample from a pregnant subject after a treatment for a disease to the pregnant subject has been administered and (ii) generate a peak representing an internal standard; a computer-readable memory comprising computer-executable instructions; and one or more processors communicatively coupled to the mass spectrometry device and configured to execute the computer-executable instructions, wherein when the one or more processors are executing the computer-executable instructions, the one or more processors are configured to carry out operations comprising: determining a peak area ratio of the drug in the extracted DBS sample to the internal standard; and identifying the administered treatment as being below an internal standard threshold when the peak area ratio of the drug in the extracted DBS sample to the internal standard is less than 1.

Provided herein are systems that include: a mass spectrometer configured to (i) generate a peak representing a drug in an extracted DBS sample from a pregnant subject after a treatment for a disease to the pregnant subject has been administered and (ii) generate a peak representing an internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the internal standard; and identifying the administered treatment as being effective when the peak area ratio of the drug in the extracted DBS sample to the internal standard is less than 1.

In some embodiments of any of the systems described herein, the peak area ratio of the drug in the extracted DBS sample to the first internal standard being less than 1 indicates that a level of the drug in the pregnant subject is non-toxic to a fetus of the pregnant subject.

In some embodiments of any of the systems described herein, the peak area ratio of the drug in the extracted DBS sample to the second internal standard being greater than 1 indicates that a level of the drug in the pregnant subject is harmful to a fetus of the pregnant subject.

In some embodiments of any of the systems described herein, the drug is a cardiac drug, an anticoagulant, a bronchodilator, an antibiotic, an anti-epileptic, an antidepressant, an antimanic agent, an antipsychotic, an antiretroviral, or an immune modulator.

Also provided herein are systems that include: a mass spectrometry device configured to (i) generate a peak representing a drug in an extracted DBS sample from a subject after a treatment for a disease has been administered and (ii) generate a peak representing an internal standard; a computer-readable memory comprising computer-executable instructions; and one or more processors communicatively coupled to the mass spectrometry device and configured to execute the computer-executable instructions, wherein when the one or more processors are executing the computer-executable instructions, the one or more processors are configured to carry out operations comprising: determining a peak area ratio of the drug in the extracted DBS sample to the internal standard; and identifying the administered treatment as being below an internal standard threshold when the peak area ratio of the drug in the extracted DBS sample to the internal standard is less than 1.

Also provided herein are systems that include: a mass spectrometer configured to (i) generate a peak representing a drug in an extracted DBS sample from a subject after a treatment for a disease has been administered and (ii) generate a peak representing an internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the internal standard; and identifying the administered treatment as being effective when the peak area ratio of the drug in the extracted DBS sample to the internal standard is less than 1.

In some embodiments of any of the systems described herein, the peak area ratio of the drug in the extracted DBS sample to the first internal standard being less than 1 indicates that a level of the drug in the subject is non-toxic to the subject.

In some embodiments of any of the systems described herein, the peak area ratio of the drug in the extracted DBS sample to the second internal standard being greater than 1 indicates that a level of the drug in the subject is harmful to the subject.

In some embodiments of any of the systems described herein, the drug is a cardiac drug, an anticoagulant, a bronchodilator, an antibiotic, an anti-epileptic, an antidepressant, an antimanic agent, an antipsychotic, an antiretroviral, or an immune modulator.

Provided herein are systems that include: a mass spectrometer configured to (i) generate a peak representing a drug in an extracted DBS sample from a pregnant subject after a treatment for multiple sclerosis to the pregnant subject has been administered, (ii) generate a peak representing a first internal standard, and (iii) generate a peak representing a second internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the first internal standard; determining a peak area ratio of the drug in the extracted DBS sample to the second internal standard; and determining that an amount of the drug in the pregnant subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are systems that include: a mass spectrometer configured to (i) generate a peak representing a drug in an extracted DBS sample from a pregnant subject after a treatment for multiple sclerosis to the pregnant subject has been administered, (ii) generate a peak representing a first internal standard, and (iii) generate a peak representing a second internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the first internal standard; determining a peak area ratio of the drug in the extracted DBS sample to the second internal standard; and identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

In some embodiments of any of the systems described herein, the peak area ratio of the drug in the extracted DBS sample to the first internal standard being less than 1 indicates that a level of the drug in the pregnant subject is non-toxic to a fetus of the pregnant subject.

In some embodiments of any of the systems described herein, the peak area ratio of the drug in the extracted DBS sample to the second internal standard being greater than 1 indicates that a level of the drug in the pregnant subject is harmful to a fetus of the pregnant subject.

In some embodiments of any of the systems described herein, the first internal standard is a minimum effective concentration of the drug.

In some embodiments of any of the systems described herein, the second internal standard is a minimum toxic concentration of the drug.

In some embodiments of any of the systems described herein, the administered treatment and the drug are teriflunomide.

Also provided herein are systems that include: a mass spectrometer configured to (i) generate a peak representing a drug in an extracted DBS sample from a pregnant subject after a treatment for a disease to the pregnant subject has been administered, (ii) generate a peak representing a first internal standard, and (iii) generate a peak representing a second internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the first internal standard; determining a peak area ratio of the drug in the extracted DBS sample to the second internal standard; and determining that an amount of the drug in the pregnant subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are systems that include: a mass spectrometer configured to (i) generate a peak representing a drug in an extracted DBS sample from a pregnant subject after a treatment for a disease to the pregnant subject has been administered, (ii) generate a peak representing a first internal standard, and (iii) generate a peak representing a second internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the first internal standard; determining a peak area ratio of the drug in the extracted DBS sample to the second internal standard; and identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

In some embodiments of any of the systems described herein, the peak area ratio of the drug in the extracted DBS sample to the first internal standard being less than 1 indicates that a level of the drug in the pregnant subject is non-toxic to a fetus of the pregnant subject.

In some embodiments of any of the systems described herein, the peak area ratio of the drug in the extracted DBS sample to the second internal standard being greater than 1 indicates that a level of the drug in the pregnant subject is harmful to a fetus of the pregnant subject.

Also provided herein are systems that include: a mass spectrometer configured to (i) generate a peak representing a drug in an extracted DBS sample from a subject after a treatment for a disease to the subject has been administered, (ii) generate a peak representing a first internal standard, and (iii) generate a peak representing a second internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the first internal standard; determining a peak area ratio of the drug in the extracted DBS sample to the second internal standard; and determining that an amount of the drug in the subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are systems that include: a mass spectrometer configured to (i) generate a peak representing a drug in an extracted DBS sample from a subject after a treatment for a disease to the subject has been administered, (ii) generate a peak representing a first internal standard, and (iii) generate a peak representing a second internal standard; a computer-readable memory comprising computer-executable instructions; and one or more processors communicatively coupled to the mass spectrometer and configured to execute the computer-executable instructions, wherein when the one or more processors are executing the computer-executable instructions, the one or more processors are configured to carry out operations comprising: determining a peak area ratio of the drug in the extracted DBS sample to the first internal standard; determining a peak area ratio of the drug in the extracted DBS sample to the second internal standard; and identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

In some embodiments of any of the systems described herein, the peak area ratio of the drug in the extracted DBS sample to the first internal standard being less than 1 indicates that a level of the drug in the subject is non-toxic to the subject.

In some embodiments of any of the systems described herein, the peak area ratio of the drug in the extracted DBS sample to the second internal standard being greater than 1 indicates that a level of the drug in the subject is harmful to the subject.

In some embodiments of any of the systems described herein, the first internal standard is a minimum effective concentration of the drug.

In some embodiments of any of the systems described herein, the second internal standard is a minimum toxic concentration of the drug.

In some embodiments of any of the systems described herein, the administered treatment and the drug are teriflunomide.

In some embodiments of any of the systems described herein, the drug is a cardiac drug, an anticoagulant, a bronchodilator, an antibiotic, an anti-epileptic, an antidepressant, an antimanic agent, an antipsychotic, an antiretroviral, or an immune modulator.

Provided herein are dried blood spot (DBS) cards including a filter paper, a pretreated region comprising at least one internal standard of a drug, wherein the at least one internal standard of the drug is deposited at a threshold level onto the pretreated region.

In some embodiments, the drug is a drug for the treatment of relapse-remitting multiple sclerosis. In some embodiments of any of the DBS cards described herein, the drug is teriflunomide.

In some embodiments of any of the DBS cards described herein, the drug is a cardiac drug, an anticoagulant, a bronchodilator, an antibiotic, an anti-epileptic, an antidepressant, an antimanic agent, an antipsychotic, an antiretroviral, or an immune modulator.

In some embodiments of any of the DBS cards described herein, the at least one internal standard threshold level is 0.02 mcg/mL of a teriflunomide. In some embodiments, the teriflunomide is [$^{2}H_{6}$]-Teriflunomide or [$^{13}C_{2}$, $^{2}H_{3}$]-Teriflunomide. In some embodiments, the teriflunomide is [$^{2}H_{6}$]-Teriflunomide. In some embodiments, the teriflunomide is [$^{13}C_{2}$, $^{2}H_{3}$]-Teriflunomide. In some embodiments, the at least one internal standard comprises a first internal standard and a second internal standard.

In some embodiments, the first internal standard is a minimum effective concentration of the drug.

In some embodiments, the second internal standard is a minimum toxic concentration of the drug. In some embodiments of any of the DBS cards described herein, the DBS card includes three or more pretreated regions comprising the at least one internal standard of the drug.

In some embodiments of any of the DBS cards described herein, the DBS card further includes patient identifying information.

Also provided herein are kits that include: a dried blood spot card including a pretreated region including at least one internal standard of a drug for a disease (e.g., multiple sclerosis) for a subject (e.g., a pregnant subject), wherein the at least one internal standard of the drug is deposited onto the pretreated region at a threshold level associated with efficacy of the drug.

In some embodiments of any of the kits described herein, the drug for the disease is a cardiac drug, an anticoagulant, a bronchodilator, an antibiotic, an anti-epileptic, an antidepressant, an antimanic agent, an antipsychotic, an antiretroviral, or an immune modulator.

In some embodiments of any of the kits described herein, the disease is multiple sclerosis. In some embodiments, the drug for multiple sclerosis is teriflunomide.

In some embodiments of any of the kits described herein, the subject is a pregnant subject.

In some embodiments, the at least one internal standard is labeled with a radioisotope, a fluorophore or a quencher.

In some embodiments of any of the kits described herein, one or more of a single-use lancet, a syringe with a needle, a container, a desiccant packet, an alcohol swab, a sterile gauze swab, a patient form, technical instructions, and an envelope.

In some embodiments, the kit includes a single-use lancet, a container, a desiccant packet, an alcohol swab, a sterile gauze swab, a patient form, technical instructions, and an envelope.

In some embodiments of any of the kits described herein, the container is a gas-impermeable sealable bag. In some embodiments of any of the kits described herein, the container is a foil bag.

In some embodiments of any of the kits described herein, the at least one internal standard is 0.02 mcg/mL of a teriflunomide.

In some embodiments of any of the kits described herein, the at least one internal standard is [$^{2}H_6$]-Teriflunomide or [$^{13}C_2$, $^{2}H_3$]-Teriflunomide.

In some embodiments of any of the kits described herein, the at least one internal standard comprises a first internal standard and a second internal standard.

In some embodiments, the first internal standard is a minimum effective concentration of the drug.

In some embodiments of any of the kits described herein, the second internal standard is a minimum toxic concentration of the drug.

As used herein, the word "a" before a noun represents one or more of the particular noun. For example, the phrase "a small molecule" represents "one or more small molecules." The term "small molecule drug", as used herein, refers to a therapeutic agent having low molecular weight that is used in the prevention, diagnosis or treatment of a pathology. The therapeutic agent is usually synthesized by organic chemistry, but may also be isolated from natural sources, such as plants, fungi, and microbes.

The term "biological drug", as used herein, refers to any therapeutic substance made or obtained from a living organism or its products that is used in the prevention, diagnosis or treatment of a pathology. Thus a biological drug or pharmaceutical is a medical drug produced using biotechnology, for example, a protein (e.g., a recombinant therapeutic protein), or a nucleic acid (e.g., DNA, RNA, or antisense oligonucleotides), used for therapeutic or in vivo diagnostic purposes.

The term "pregnant" or "pregnancy", as used herein, refers to the state of a subject having, displaying or having been determined to have a concentration of human placental lactogen, or a relevant fragment thereof, human chorionic gonadotrophin (hCG) hormone, or a relevant fragment therefore, in a biological sample (e.g., urine, blood, fluid) obtained from said subject associated with a gestational stage (e.g., 6 weeks or less, 6 to 9 weeks, 10 to 12 weeks, 13-16 weeks, 17-24 weeks).

The term "biological fluid" means any fluid obtained from a mammalian subject (e.g., a human) (e.g., blood, plasma, serum, or other blood fractions, urine, saliva, breast milk, or tears). In preferred embodiments, the biological fluid is urine, blood, serum or plasma.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences and database entries, and other references mentioned herein are incorporated by reference in their entirety. In case of conflict, the present specification, including definitions, will control.

Other aspects, features, and advantages of the invention will be apparent from the following detailed description and figures, and from the claims.

Figure 1:
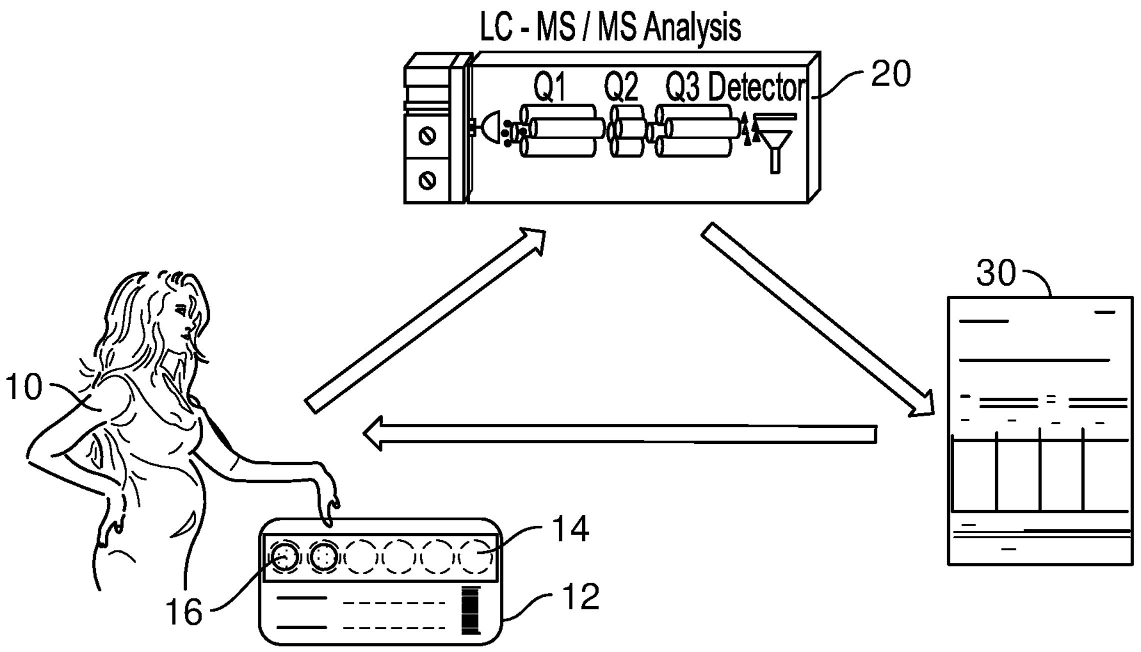
FIG. 1 is a schematic representation of one example of a testing system and process used to determine the plasma teriflunomide concentration in a pregnant subject.

This disclosure relates to systems and methods for monitoring drug plasma concentrations (e.g., plasma teriflunomide concentrations) using a dried blood spot (DBS) in subjects (e.g., in pregnant subjects or subjects planning a pregnancy).

Multiple sclerosis is progressive and chronic demyelinating disease of the central nervous system that affects T cells (e.g., helper T cells) and B cells. Typically, multiple sclerosis is diagnosed in young adulthood, e.g., in people between the ages of 20 and 50. Four stages of multiple sclerosis have been identified: clinically isolated syndrome (CIS), relapsing-remitting multiple sclerosis (RRMS), secondary progressive multiple sclerosis (SPMS), and primary progressive multiple sclerosis (PPMS). CIS is described as an episode of neurologic symptoms lasting at least 24 hours, in which a subject most often displays numbness or tingling in the arms, legs or face, blurred vision, vertigo, and/or problems with balance (Effendi, Noro Psikiyatr Ars., 2015, 52(Suppl 1): S1-S11). RRMS is defined by increasing neurologic exacerbations that are followed by a period of partial or complete remission. During these neurologic exacerbations, activated immune cells (e.g., T cells and B cells) cause localized areas of inflammation and damage, which lead to symptoms of multiple sclerosis. RRMS can last on average 10 years after which 50% of subjects with RRMS develop permanent disability and will develop SPMS (Lugaresi et al., Neuropsychiatr Dis Treat, 2013, 9: 893-914). 90% of subjects who experience RRMS develop SPMS within 25 years. SPMS is characterized by a progressive worsening of neurologic function that may include intervals of relapse or remission. Roughly 15% of subjects diagnosed with multiple sclerosis have PPMS (Ontaneda and Fox, Curr Opin Neurol., 2015, 28(3): 237-243).

Various medications exist to treat the exacerbations (i.e., inflammatory attacks associated with multiple sclerosis), such as injectable medications, oral medications, and infused medications. Non-limiting examples of injectable medications for multiple sclerosis include: interferon beta-1a (e.g., AVONEX®, REBIF®, PLEGRIDY®), interferon beta-1b (e.g., BETASERON®, EXTAVIA®), and glatiramer acetate (e.g., COPAXONE®, GLATOPA®). Non-limiting examples of oral medications for multiple sclerosis include: teriflunomide (e.g., AUBAGIO®), fingolimod (e.g., GILENYA®), cladribine (e.g., MAVENCLAD®), siponimod (e.g., MAYZENT®), dimethyl fumarate (e.g., TECFIDERA®, VUMERITY™). Non-limiting infused medications include: alemtuzumab (e.g., LEMTRADA®), mitoxantrone (e.g., NOVANTRONE®), ocrelizumab (e.g., OCREVUS®), and natalizumab (e.g., TYSABRI®). Other medications that can be used to treat multiple sclerosis include: methylprednisolone (e.g., SOLU-MEDROL®), prednisone (e.g., DELTASONE®), and adrenocorticotropic hormone (ACTH) (e.g., H.P. ACTHAR® gel). See, e.g., Bar-Or, et al., Drugs 2014, 74(6): 659-674.

Teriflunomide (also known as (Z)-2-cyano-alpha, alpha, alpha-trifluoro-3-hydroxy-p-crotonotoluidide) is an immunomodulatory drug that blocks the mitochondrial enzyme, dihydroorotate dehydrogenase, which is required for pyrimidine de novo synthesis. Without directly causing cell death, teriflunomide slows down the proliferation of active T and B lymphocytes. Teriflunomide can be administered as an active agent or as leflunomide. Leflunomide is converted into teriflunomide via opening of the isoxazole ring upon administration in vivo. Teriflunomide, sold under the name AUBAGIO®, was initially prescribed to patients suffering from multiple sclerosis (e.g., relapsing-remitting multiple sclerosis) for once a day oral treatment. In some examples, teriflunomide is recommended at an oral dose of 7 mg or 14 mg once a day. During pregnancy, it may be beneficial to keep plasma teriflunomide concentration less than 0.02 mcg/mL.

Example System and Process Used to Determine the Plasma Teriflunomide Concentration in a Pregnant Subject FIG. 1 graphically depicts one example of a testing system and process used to determine the plasma teriflunomide concentration in a pregnant subject 10. The process to determine the plasma teriflunomide concentration can be divided into several steps: (1) collection of blood onto a dried blood spot (DBS) card; (2) drying of bloodstained DBS card; (3) storage and transportation of bloodstained DBS card; (4) extraction of teriflunomide and ISTD from DBS card; and (5) analyses of extracted teriflunomide samples.

As shown in FIG. 1, the pregnant subject 10 first deposits droplets of her blood onto a DBS card 12 having regions 14 that are pre-treated with stable-labeled Internal Standard [$^{13}C_2$, $^{2}H_3$]-Teriflunomide (ISTD). Any of various techniques can be used for depositing the subject's blood onto the DBS card 12, such using a finger prick, a palm of the hand prick, an arm prick, a calf prick, or a thigh prick. In many cases, a finger prick technique is used. Using that technique, the subject (or the subject's physician, nurse, or other medical professional) pricks the subject's finger with a lancet device (e.g., a single-use auto-disabling lancet, a capillary blood specimen collection device, or a re-usable lancet). The subject 10 then positions the punctured finger over one of the pre-printed circles indicating to users the pre-treated regions 14 on the DBS card 12 such that a droplet of blood drips onto the pre-treated region 14, creating a bloodstain 16 on that pre-printed circle indicating the pre-treated region 14 of the DBS card 12. Due to the amount of ISTD used to form the pre-treated regions 14, the blood droplets tend to spread over substantially the entire surface of the pre-treated region 14 of the DBS card 12. Blood droplets can be dripped onto each of the pre-circled pre-treated regions 14 of the DBS card to create multiple bloodstains 16. While only three of the six pre-treated regions 14 are shown with bloodstains 16 in FIG. 1, the user would typically deposit blood droplets onto each of the pre-treated regions 14 before sending the DBS card 12 out for analysis. To dry the bloodstains, the DBS card 12 is left at room temperature for at least 2 hours. In many cases, the DBS card 12 is left at room temperature for 3-4 hours or overnight.

Once the bloodstains 16 have dried, the bloodstained DBS card 12 is mailed or otherwise sent to a facility with a laboratory (e.g., a clinic, a hospital, or a research institute) that includes a liquid chromatography-mass spectrometry (LC-MS/MS) system 20 for analysis. Because the LC-MS/MS system 20 need not be highly specialized, in some cases, a DBS processing center (e.g., a clinic, a hospital, or a research institute) may be located in the same building or office space where the blood was collected. Advantageously, as explained below, any facility (e.g., a laboratory) equipped with a high performance liquid chromatography mass spectrometer (e.g., a liquid chromatography tandem-mass spectrometer) can be used to determine the plasma teriflunomide level in the subject 10 without the need to use a validated method. While certain current plasma bioanalytical methods allow precise determination of plasma teriflunomide concentrations, those blood samples must generally be sent to a specific vendor that is equipped to prepare the plasma from blood samples and have access to a validated method and laboratory. The systems and methods described herein can provide subjects with results faster and less expensively than many of the current bioanalytical methods.

In some embodiments, processing of the bloodstained DBS card 12 is delayed until a later date. For example, a bloodstained DBS card 12 may be placed into a gas-impermeable sealable bag (e.g., a foil bag) containing one or more desiccant sachets to protect the bloodstained DBS card 12 from moisture. Once the bloodstained DBS card 12 is placed in the gas-impermeable sealable bag (e.g., a foil bag), the bag containing the bloodstained DBS card may be stored at room temperature for up to 4 months.

Figure 2:
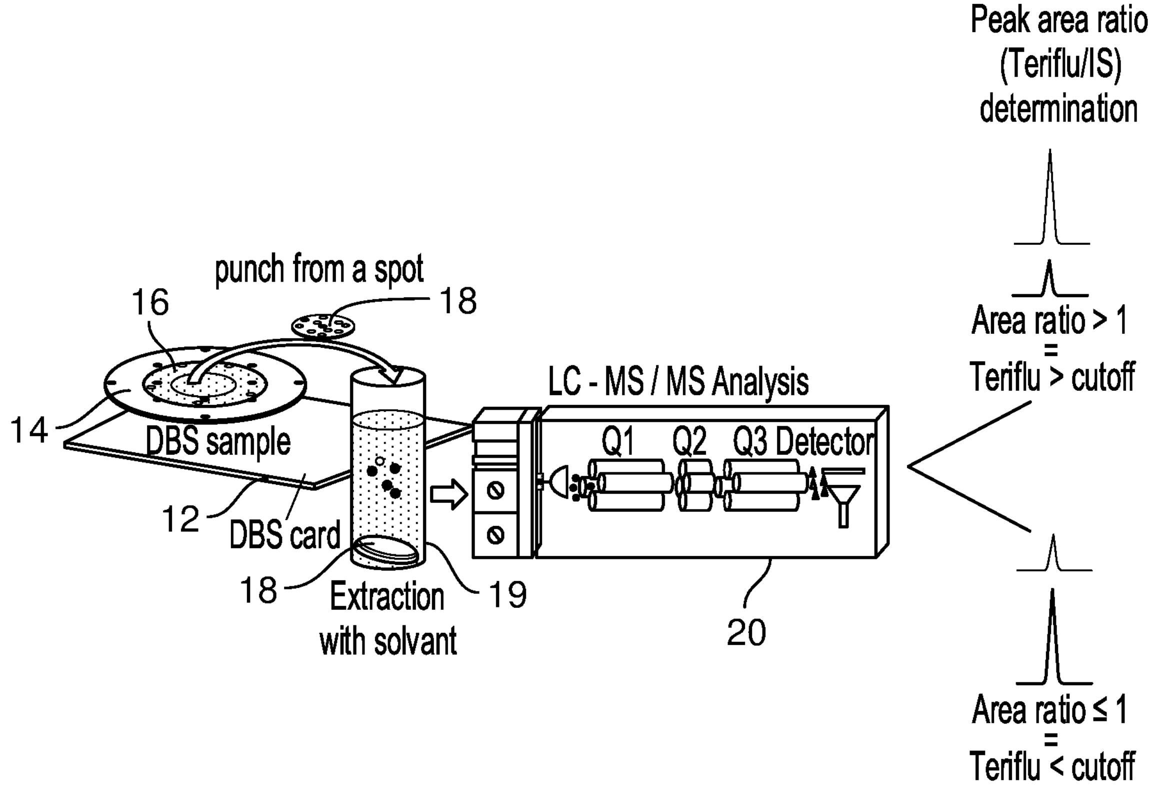
FIG. 2 is a schematic representation of an embodiment of a method of analyzing a dried blood spot (DBS) sample using a high performance liquid chromatography mass spectrometer (LC-MS/MS) based on a peak area ratio using a single internal standard (ISTD).

Referring also to FIG. 2, which graphically illustrates the mass spectrometry system 20 and analysis in greater detail, once the bloodstained DBS card 12 arrives at the laboratory, one or more portions 18 of the bloodstained pre-treated regions 16 are punched out and then dropped into a vessel or tube 19 containing solution (e.g., a solution including methanol) to extract teriflunomide and ISTD from the card. The diameter of the punched out portions 18 can range from 2-8 mm. In some embodiments, 6-mm diameter portions are punched out from the center of the bloodstained pre-treated regions 16. Any of various punching techniques can be used.

In some cases, the one or more portions 18 of the bloodstained pre-treated regions 16 are punched out using a single-use 6 mm punching device from the center of the bloodstained pre-treated region 16. Examples of suitable punching devices that can be used include manual punching devices, such as the Harris Micro-Punch (Fisher Scientific), and semi-automated punching devices, such as those available from TOMTEC, Inc.

To extract a drug (e.g., teriflunomide) and ISTD from the bloodstained DBS card 12, the punched bloodstained region of the DBS card is extracted using a volume of methanol (e.g., 200 μL of methanol) contained in the tube 19. The extracted samples can then be vortexed for about 20 minutes (e.g., 15 minutes, 16 minutes, 18 minutes, 20 minutes, 22 minutes, 24 minutes, or 25 minutes), and centrifuged for about 5 minutes at about 10,000 rotations per minute (rpm) (e.g., about 12,000 rpm, 13,000 rpm, 14,000 rpm, or 15 rpm). After centrifugation, an aliquot of the supernatant (i.e., methanol containing teriflunomide, ISTD and other soluble blood components in organic solvent) is injected onto the high performance liquid chromatography mass spectrometer system 20.

Still referring to FIGS. 1 and 2, once the subject's DBS have been extracted from the DBS card 12 and collected, mass spectrometry is performed on the extracted DBS sample. Mass spectrometry is likewise performed on the ISTD. Chromatography can be performed on an Agilent Zorbax Eclipse XDB-C8 analytical column with 3.5 μm particle size (4.6 mm internal diameter, 50 mm length) at a flow rate of 0.7 mL/min with mobile phases consisting of a mixture of water/acetonitrile (vol/vol) containing 0.1% acetic acid. Optimal chromatographic separation can be achieved by running for 4.5 minutes isocratically. The column can be maintained at 40° C. with the column effluent delivered to the mass spectrometer interface without splitting. The mass spectrometric conditions consist of a Sciex AP14000 triple quadrupole mass spectrometer (MDS SCIEX; Applied Biosystems, Concord, ON, Canada) controlled by Analyst 1.4.2 software. The mass spectrometer can be operated in the negative multiple reaction monitoring mode by using a Turbo Ion Spray source. In some embodiments, the LC-MS/MS system 20 used to analyze teriflunomide and ISTD samples includes a pump (e.g., a Shimadzu LC-20AD pump), an autosampler (e.g., a SIL-20AC autosampler), and an oven (e.g., a CTO-20AC oven). The area ratio of teriflunomide/ISTD is determined for each punched out portion 18 of the bloodstained 16 pre-treated region 14 of the DBS card 12. If the area ratio is less than 1, the teriflunomide concentration is considered less than the cutoff (i.e., less than 0.02 mcg/mL). If the area ratio is greater than 1, the teriflunomide concentration is considered to be greater than the cutoff (i.e., greater than 0.02 mcg/mL). In the latter case, the concentration of teriflunomide can be estimated by multiplying the concentration of the cutoff (20 ng/mL) by the area ratio. Based on results of the mass spectrometry analysis, a determination can be made about whether the level of teriflunomide in the subject should be increased/decreased. For example, if the area ratio is less than 1, the teriflunomide concentration is considered less than the cutoff (i.e., the teriflunomide concentration is less than 0.02 mcg/mL in the tested sample), and therefore the level of teriflunomide in the subject can be increased. The subject can take an additional dose of teriflunomide.

If the area ratio is greater than 1, the teriflunomide concentration is considered greater than the cutoff (i.e., the teriflunomide concentration is greater than 0.02 mcg/mL in the tested sample), and therefore the level of teriflunomide in the subject should be decreased. The subject should not take an additional dose of teriflunomide, and/or should continue to monitor the level of teriflunomide after a period of time (e.g., after 2 weeks, after 3 weeks, after 4 weeks, after 6 weeks, after 8 weeks, or after 10 weeks). In certain cases, active steps, such as administering cholestryramine or activated charcoal to the subject, may be taken to reduce the level of teriflunomide in the subject. In some cases, for example, 8 g of cholestryramine can be administered to the subject every 8 hours for 11 days. In other examples, 50 g of oral activated charcoal powder can be administered to the subject every 12 hours for 11 days.

Figure 3:
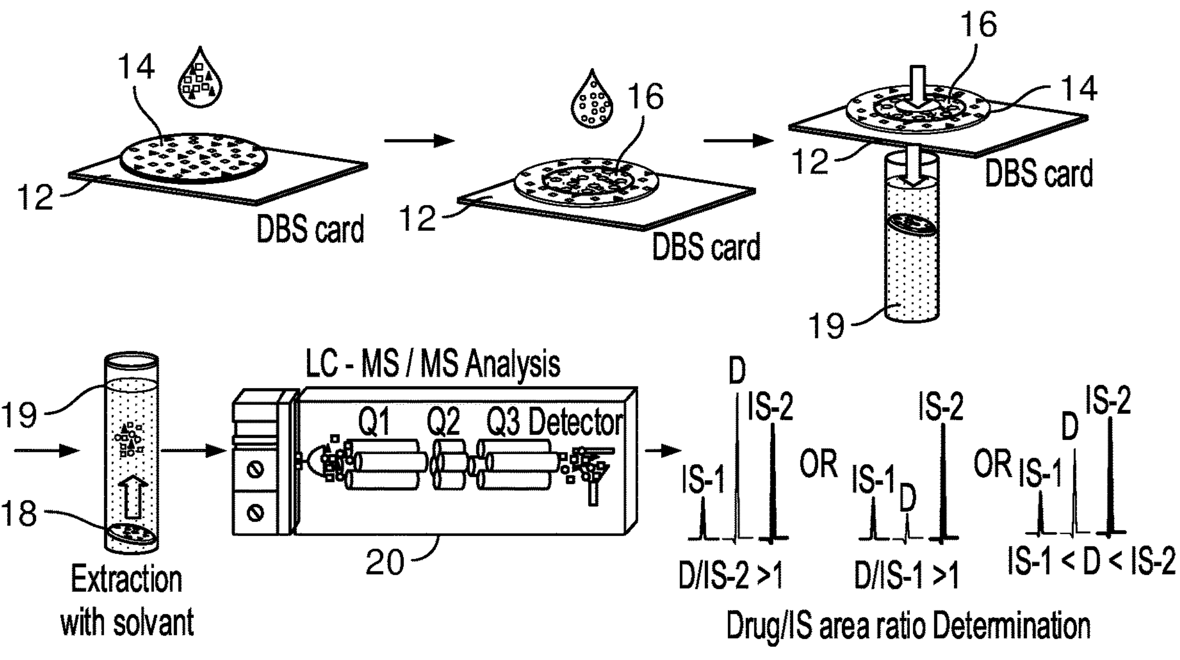
FIG. 3 is a schematic representation of an embodiment of a method of analyzing a DBS sample using an LC-MS/MS based on a peak area ratio using two ISTDs.

FIG. 3 graphically illustrates an alternative technique that can be carried out by the LC-MS/MS system 20, which involves spotting each pretreated region on the DBS card 14 with a stable-labeled internal standard [$^2H_6$]-drug (ISTD) (IS-1) and a stable-labeled internal standard [$^{13}C_2$, $^2H_3$]-drug (ISTD) (IS-2). IS-1 is a low internal standard concentration (e.g., an ISTD concentration of minimum effective concentration) and IS-2 is a high internal standard concentration (e.g., an ISTD concentration of minimum toxic concentration or an ISTD concentration of maximum therapeutic concentration). The process shown in FIG. 3 is essentially identical to the process shown in FIG. 2 except for the analyses of extracted DBS samples. Therefore, only the analyses will be discussed in detail.

Still referring to FIG. 3, if the area ratio of drug/IS-1 is less than 1, the drug concentration is considered less than the minimum effective concentration, and therefore the dose level of the drug in the subject should be increased. The subject should take an additional dose of the drug.

If the area ratio of drug/IS-2 is greater than 1, the drug concentration is considered greater than the minimum toxic concentration or greater than the maximum therapeutic concentration, and therefore the dose level of the drug in the subject should be decreased. The subject should not take an additional dose of the drug, and/or should continue to monitor the level of the after a period of time as defined by the subject's physician, nurse, or other medical professional (e.g., after 2 weeks, after 3 weeks, after 4 weeks, after 6 weeks, after 8 weeks, or after 10 weeks).

If the area ratio of drug/IS-1 is greater than 1 and the area ratio of drug/IS-2 is less than 1, the drug concentration is considered within the therapeutic range or therapeutic window, and therefore the dose of the drug in the subject can be maintained or adjusted by the subject's physician, nurse, or other medical professional.

The determination of the peak areas and peak area ratios as well as the various other analyses described with reference to FIGS. 2 and 3 can be carried out by a computer of the LC-MS/MS system 20. The computer can include one or more processors and one or more databases that allow the computer to carry out the analyses. The computer can also be connected to a network that allows the data and/or analysis results to be transmitted from the LC-MS/MS system 20 to other locations, such as a remote server.

Referring again to FIG. 1, the mass spectrometry results are configured in a report 30 that is sent to the pregnant subject 10 and/or to a medical professional who is treating the pregnant subject 10. The report 30 can be a printed report that is mailed to the pregnant subject 10 or to her medical professional, or it can be an electronic file including data that is electronically transmitted to the pregnant subject 10 or to her medical professional. The information provided in the report can be used by the pregnant subject's medical professional to base future treatments on the level of teriflunomide determined to be in the subject's blood.

Figure 4:
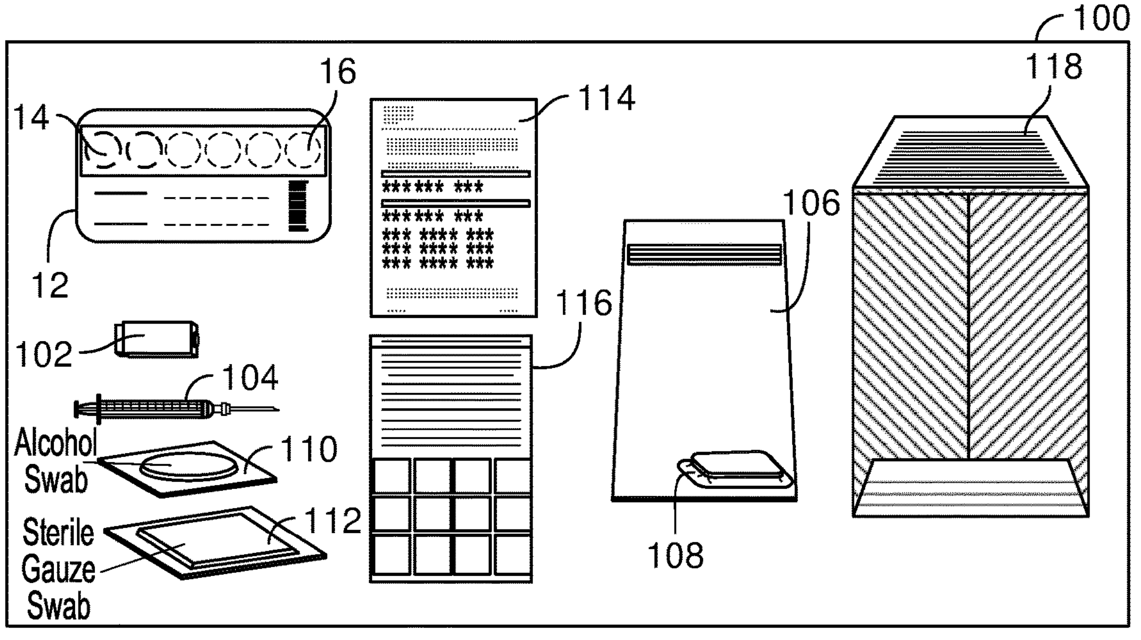
FIG. 4 is a schematic representation of a kit that can be used for used determining the plasma teriflunomide concentration in a pregnant subject.

FIG. 4 illustrates a kit 100 that can be provided to pregnant subjects or to medical professionals who treat pregnant subjects for testing plasma concentrations (e.g., plasma teriflunomide concentrations) of the subjects. The kit 100 includes the DBS card 12, a single-use lancet (e.g., a single-use finger pricking tool) 102 that can be used to puncture the subject's skin, a syringe with a needle 104 that can be used for venipuncture, a container (e.g., a gas-impermeable sealable bag (e.g., a foil bag)) 106 with a desiccant packet 108, an alcohol swab 110, a sterile gauze swab 112, a patient form 114, technical instructions for how to collect a blood sample 116, and an envelope (e.g., a stamped envelope) 118 that can used to mail a bloodstained DBS card to a laboratory for analysis. The various components of the kit 100 can be used to carry out the process described above for testing plasma teriflunomide concentrations of pregnant subjects.

When a pregnant subject being treated for multiple sclerosis, for example, becomes pregnant or expresses an interest in becoming, her physician may use the kit 100 to collect dried blood spots samples from the subject and then send those samples to a laboratory for testing. Typically, the physician will clean the a prick site of the subject using the alcohols swab 110 and then use the lancet 102 to collect blood samples from the subject in the manner described above. However, in some cases, it may be desirable or necessary to collect blood from the subject via venipuncture by using the syringe 104. After collecting the blood spot samples, the dried bloodstained DBS card 12 is deposited into the bag 106 and the bag is sealed. The bag 106 containing the bloodstained DBS card 12 is then placed in the envelope 118 along with the patient form 114 filled out to include identifying information of the subject, billing information, etc.

Figure 5:
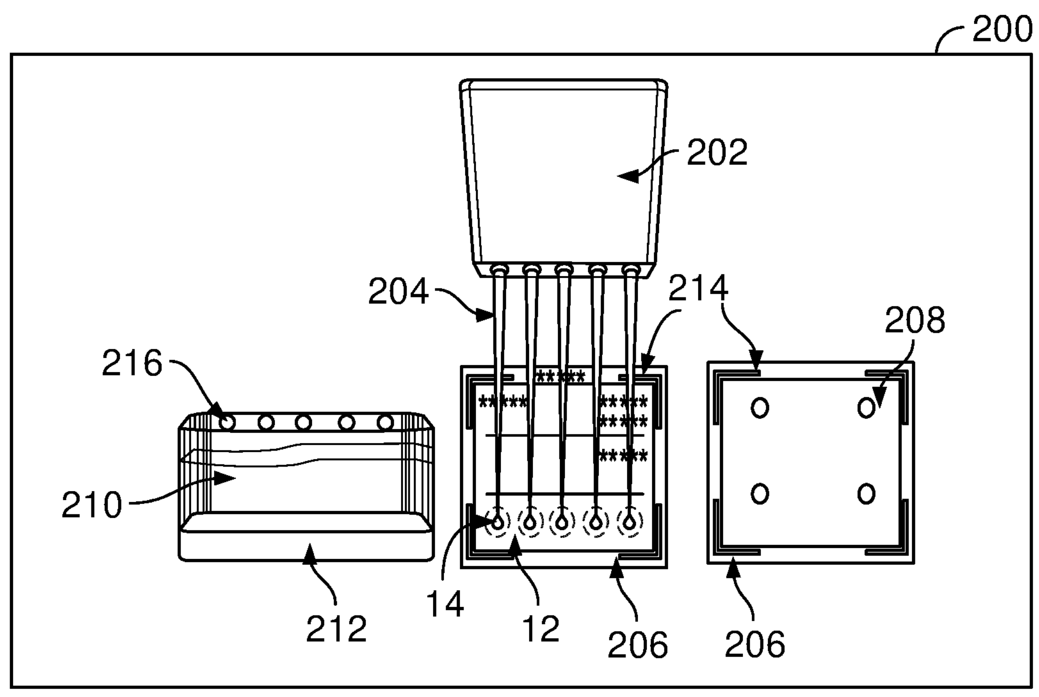
FIG. 5 is a schematic representation showing a system for pretreating DBS cards with ISTD.

FIG. 5 illustrates a system 200 that can be used to produce the pre-treated DBS cards 12. The pre-treated DBS cards can be made using various types of filter paper, such as Whatman 903 Protein saver filter paper and Perkin Elmer 226 filter paper. The filter paper is generally not impregnated with chemicals and does not have a wraparound cover. Non-limiting types of filter papers that can be used include PerkinElmer 226 Bioanalysis RUO Card #226-1004 or PerkinElmer 226-5 Spot Ruo Card #226-1002.

Still referring to FIG. 5, the system 200 includes an automatic pipette head 202, micro-tips 204 extending downwardly from the automatic pipette head 202, a rack 206 for holding a DBS card, a DBS card elevator (e.g., protrusions) 208 to prevent contact between the DBS card 12 and the rack's base, a container 210 for the ISTD solution having a lid 216 with through holes for receiving the micro-tips 204, and a preform that can be treated to form DBS card 12. A card fixing edge 214 of the rack 206 serves to center the DBS card 12 within the rack 206. The automatic pipette head 202 is equipped with variable tip spacing to use with different types of DBS cards and with anti-droplet control and surface detection. The ISTD solution in the container 210 includes ISTD dissolved in methanol to a concentration of 80 ng/mL. In some examples, a highly concentrated stock solution of ISTD is first prepared in dimethyl sulfoxide, then 1 volume of this stock solution is diluted in 200 volumes of methanol solution, which can be used as the ISTD solution that is poured into the container 210. The container for the ISTD solution is equipped with a Peltier temperature control system 212 to maintain the temperature of the ISTD solution between 10° C. and 15° C. The system 200 shown in FIG. 5 is able to deposit, without significant splashing, a precise volume of ISTD solution on the surface of the filter paper in the center of the deposit zone to form the pretreated region 14. Each micro-tip 204 is connected to an individual micro-syringe allowing the distribution of an accurate micro-volume of ISTD solution ranging from 5 μL to 25 μL.

Figure 6:
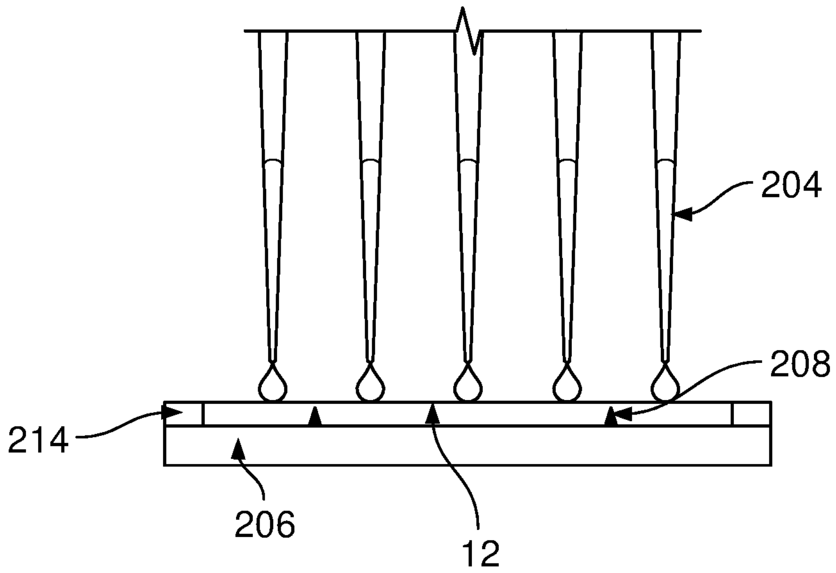
FIG. 6 is a schematic representation showing an automatic pipette head and micro-tips of the system of FIG. 5 depositing the ISTD onto the DBS card.

Referring also to FIG. 6, to produce the DBS cards 12, a preform DBS card formed of non-treated filter paper is placed on the rack 206. The automatic pipette head 202 is positioned over the ISTD container 210 and then lowered so that the micro-tips 204 become immersed in the ISTD solution. The micro-syringes associated with the micro-tips 204 are then operated to draw a precise volume of the ISTD solution into each of the micro-tips 204. The automatic pipette head 202 is then raised to remove the micro-tips 204 from the container 210, and then moved laterally to position the micro-tips 204 over designated regions of the preform DBS card. The micro-syringes are then operated to dispense a desired volume of the ISTD solution onto the filter paper to form the pretreated regions 14.

When it is desired to pretreat the preform DBS card with multiple different ISTDs (e.g., for forming the DBS card used in process described with respect to FIG. 2 above), one container containing a solution of different ISTD (e.g., a mixture of [$^{13}C_2$, $^{2}H_3$]-teriflunomide and [$^{2}H_4$]-teriflunomide) can be provided and the automatic pipette head 202 and micro-tips 204 can be maneuvered to draw the ISTD solution into the micro-tips 204 and then deposit a precise volume of the ISTDs solution onto the preform DBS card.

The regions on the DBS card 12 that are to be pre-treated with ISTD 14 are typically spotted with ISTD solution at a defined concentration using the micro-tips 204 of the automatic pipette head 202. The volume of ISTD solution to be spotted depends on the diameter of the pre-treated region 14. For example, a pre-treated region 14 with a circle diameter of 13 mm can be spotted with 20 μL of ISTD. A pre-treated region 14 with a circle diameter of 9 mm can be spotted with 15 μL of ISTD. The diameter of the pre-treated ISTD region 14 can be selected to be slightly greater than the diameter of the expected diameter of the bloodstain 16 to ensure that a precise, desired amount of blood and ISTD are included in the punched out portions 18 of the DBS card 12. The above-described process ensures that the ISTD is spread homogenously across the filter paper in the pretreated regions 14 of the DBS card 12.

Methods of Monitoring Treatment of Multiple Sclerosis

Provided herein are methods of monitoring treatment for multiple sclerosis in a pregnant subject. In some examples, these methods include: (a) extracting a drug (e.g., teriflunomide) from a dried blood spot (DBS) sample, the dried blood sample being from a pregnant subject after a treatment for multiple sclerosis to the pregnant subject has been administered; (b) performing mass spectrometry on the extracted DBS sample; (c) determining a peak area ratio of the drug (e.g., teriflunomide) in the extracted DBS sample to an internal standard; and (d) identifying the administered treatment as being below an internal standard threshold when the peak area ratio of the drug in the extracted DBS sample to the internal standard is less than 1.

Also provided herein are methods of monitoring treatment for multiple sclerosis in a pregnant subject that include: (a) extracting a drug from a dried blood spot (DBS) sample, the dried blood sample being from a pregnant subject after a treatment for multiple sclerosis to the pregnant subject has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) determining that an amount of the drug in the pregnant subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Some embodiments further include recording the monitored multiple sclerosis status of the pregnant subject's medical record (e.g., improving or static multiple sclerosis status of the pregnant subject's medical record) (e.g., a computer readable medium). Some examples further include informing the subject, the subject's family and/or the subject's primary care physician or attending physician of the pregnant subject's status after the administered treatment. Some embodiments further include authorization of a refill of an administered treatment. Some embodiments include discharging a pregnant subject from an inpatient facility (e.g., hospital) based on identification of the pregnant subject having improving or static multiple sclerosis.

Methods of Determining the Efficacy of a Treatment of Multiple Sclerosis

Provided herein are methods of determining the efficacy of treatment for multiple sclerosis in a pregnant subject. In some examples, these methods include: (a) extracting a drug (e.g., teriflunomide) from a dried blood spot (DBS) sample, the dried blood sample being from a pregnant subject after a treatment for multiple sclerosis to the pregnant subject has been administered; (b) performing mass spectrometry on the extracted DBS sample; (c) determining a peak area ratio of the drug (e.g., teriflunomide) in the extracted DBS sample to an internal standard; and (d) identifying the administered treatment as being effective when the peak area ratio of the drug in the extracted DBS sample to the internal standard is less than 1.

Also provided herein are methods of determining efficacy of treatment for multiple sclerosis in a pregnant subject that include: (a) extracting a drug from a dried blood spot (DBS) sample, the dried blood sample being from a pregnant subject after a treatment for multiple sclerosis to the pregnant subject has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Some embodiments of the methods described herein further include after (e): (f) administering an additional dose of teriflunomide to the pregnant subject.

Some embodiments of any of the methods further include a step of selecting a pregnant subject having multiple sclerosis or diagnosing a pregnant subject as having multiple sclerosis (e.g., using any of the methods of diagnosing multiple sclerosis known in the art). In some embodiments, a pregnant subject having multiple sclerosis can have previously been administered a treatment for multiple sclerosis and the treatment was unsuccessful.

Some embodiments further include recording the identified efficacy of the administered treatment in the subject's medical record (e.g., a computer readable medium). Some examples further include informing the subject, the subject's family and/or the subject's primary care physician or attending physician of the identified efficacy of the administered treatment. Some embodiments further include authorization of a refill of an administered treatment identified as being effective.

The period of time between treatment and testing can be e.g., between 1 day and 7 days, between 1 day and 5 days, between 1 day and 3 days, between 1 and 2 days, between 2 and 7 days, between 2 and 4 days, between 3 and 4 days, or between 5 and 7 days.

Methods of Monitoring Treatment of a Disease

Provided herein are methods of monitoring treatment for a disease in a subject (e.g., a pregnant subject). In some examples, these methods include: (a) extracting a drug (e.g., a cardiac drug, an anticoagulant, a bronchodilator, an antibiotic, an anti-epileptic, an antidepressant, an antimanic agent, an antipsychotic, an antiretroviral, or an immune modulator) from a dried blood spot (DBS) sample, the dried blood sample being from a subject (e.g., a pregnant subject) after a treatment for a disease has been administered; (b) performing mass spectrometry on the extracted DBS sample; (c) determining a peak area ratio of the drug in the extracted DBS sample to an internal standard; and (d) identifying the administered treatment as being below an internal standard threshold when the peak area ratio of the drug in the extracted DBS sample to the internal standard is less than 1.

Also provided herein are methods of monitoring treatment for a disease in a subject (e.g., a pregnant subject) that include: (a) extracting a drug (e.g., a cardiac drug, an anticoagulant, a bronchodilator, an antibiotic, an anti-epileptic, an antidepressant, an antimanic agent, an antipsychotic, an antiretroviral, or an immune modulator) from a dried blood spot (DBS) sample, the dried blood sample being from a subject (e.g., a pregnant subject) after a treatment for a disease has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) determining that an amount of the drug in the subject (e.g., the pregnant subject) is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Some embodiments further include recording the monitored disease status of the subject's (e.g., the pregnant subject) medical record (e.g., improving or static disease status of the subject's medical record) (e.g., a computer readable medium). Some examples further include informing the subject, the subject's family and/or the subject's primary care physician or attending physician of the subject's status after the administered treatment. Some embodiments further include authorization of a refill of an administered treatment. Some embodiments include discharging a subject from an inpatient facility (e.g., hospital) based on identification of the subject having improving or static disease status.

Methods of Determining the Efficacy of a Treatment of a Disease

Provided herein are methods of determining the efficacy of treatment for a disease in a subject (e.g., a pregnant subject). In some examples, these methods include: (a) extracting a drug (e.g., a cardiac drug, an anticoagulant, a bronchodilator, an antibiotic, an anti-epileptic, an antidepressant, an antimanic agent, an antipsychotic, an antiretroviral, or an immune modulator) from a dried blood spot (DBS) sample, the dried blood sample being from a subject (e.g., a pregnant subject) after a treatment for a disease has been administered; (b) performing mass spectrometry on the extracted DBS sample; (c) determining a peak area ratio of the drug in the extracted DBS sample to an internal standard;

and (d) identifying the administered treatment as being effective when the peak area ratio of the drug in the extracted DBS sample to the internal standard is less than 1.

Also provided herein are methods of determining efficacy of treatment for a disease in a subject (e.g., a pregnant subject) that include: (a) extracting a drug (e.g., a cardiac drug, an anticoagulant, a bronchodilator, an antibiotic, an anti-epileptic, an antidepressant, an antimanic agent, an antipsychotic, an antiretroviral, or an immune modulator) from a dried blood spot (DBS) sample, the dried blood sample being from a subject (e.g., a pregnant subject) after a treatment for a disease has been administered; (b) performing mass spectrometry on the extracted DBS sample; (c) determining a peak area ratio of the drug in the extracted DBS sample to a first internal standard; (d) determining a peak area ratio of the drug in the extracted DBS sample to a second internal standard; and (e) identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Some embodiments of the methods described herein further include after (e): (f) administering an additional dose of the drug to the subject (e.g., the pregnant subject).

Some embodiments of any of the methods further include a step of selecting a subject having a disease or diagnosing a subject as having a disease (e.g., using any of the methods of diagnosing known in the art). In some embodiments, a subject having a disease can have previously been administered a treatment for the disease and the treatment was unsuccessful.

Some embodiments further include recording the identified efficacy of the administered treatment in the subject's medical record (e.g., a computer readable medium). Some examples further include informing the subject, the subject's family and/or the subject's primary care physician or attending physician of the identified efficacy of the administered treatment. Some embodiments further include authorization of a refill of an administered treatment identified as being effective.

The period of time between treatment and testing can be e.g., between 1 day and 7 days, between 1 day and 5 days, between 1 day and 3 days, between 1 and 2 days, between 2 and 7 days, between 2 and 4 days, between 3 and 4 days, or between 5 and 7 days.

Systems

Provided herein are systems that include: a mass spectrometry device configured to (i) generate a peak representing a drug (e.g., teriflunomide) in an extracted dried blood spot (DBS) sample from a pregnant subject after a treatment for multiple sclerosis to the pregnant subject has been administered and (ii) generate a peak representing an internal standard; a computer-readable memory including computer-executable instructions; and one or more processors communicatively coupled to the mass spectrometry device and configured to execute the computer-executable instructions, wherein when the one or more processors are executing the computer-executable instructions, the one or more processors are configured to carry out operations including: determining a peak area ratio of the drug in the extracted DBS sample to the internal standard; and identifying the administered treatment as being below an internal standard threshold when the peak area ratio of the drug in the extracted DBS sample to the internal standard is less than 1.

Also provided herein are systems that include: a mass spectrometer configured to (i) generate a peak representing a drug (e.g., teriflunomide) in an extracted dried blood spot (DBS) sample from a pregnant subject after a treatment for multiple sclerosis to the pregnant subject has been administered and (ii) generate a peak representing an internal standard; a computer-readable memory including computer-executable instructions; and one or more processors communicatively coupled to the mass spectrometer and configured to execute the computer-executable instructions, wherein when the one or more processors are executing the computer-executable instructions, the one or more processors are configured to carry out operations including: determining a peak area ratio of the drug in the extracted DBS sample to the internal standard; and identifying the administered treatment as being effective when the peak area ratio of the drug in the extracted DBS sample to the internal standard is less than 1.

Also provided herein are systems that include: a mass spectrometer configured to (i) generate a peak representing a drug in an extracted dried blood spot (DBS) sample from a pregnant subject after a treatment for multiple sclerosis to the pregnant subject has been administered, (ii) generate a peak representing a first internal standard, and (iii) generate a peak representing a second internal standard; a computer-readable memory including computer-executable instructions; and one or more processors communicatively coupled to the mass spectrometer and configured to execute the computer-executable instructions, wherein when the one or more processors are executing the computer-executable instructions, the one or more processors are configured to carry out operations including: determining a peak area ratio of the drug in the extracted DBS sample to the first internal standard; determining a peak area ratio of the drug in the extracted DBS sample to the second internal standard; and determining that an amount of the drug in the pregnant subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are systems that include: a mass spectrometer configured to (i) generate a peak representing a drug in an extracted dried blood spot (DBS) sample from a pregnant subject after a treatment for multiple sclerosis to the pregnant subject has been administered, (ii) generate a peak representing a first internal standard, and (iii) generate a peak representing a second internal standard; a computer-readable memory including computer-executable instructions; and one or more processors communicatively coupled to the mass spectrometer and configured to execute the computer-executable instructions, wherein when the one or more processors are executing the computer-executable instructions, the one or more processors are configured to carry out operations including: determining a peak area ratio of the drug in the extracted DBS sample to the first internal standard; determining a peak area ratio of the drug in the extracted DBS sample to the second internal standard; and identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are systems that include: a mass spectrometry device configured to (i) generate a peak representing a drug (e.g., a cardiac drug, an anticoagulant, a bronchodilator, an antibiotic, an anti-epileptic, an antidepressant, an antimanic agent, an antipsychotic, an antiretroviral, or an immune modulator) in an extracted dried blood spot (DBS) sample from a subject (e.g., a pregnant subject) after a treatment for a disease has been administered and (ii) generate a peak representing an internal standard; a computer-readable memory including computer-executable instructions; and one or more processors communicatively coupled to the mass spectrometry device and configured to execute the computer-executable instructions, wherein when the one or more processors are executing the computer-executable instructions, the one or more processors are configured to carry out operations including: determining a peak area ratio of the drug in the extracted DBS sample to the internal standard; and identifying the administered treatment as being below an internal standard threshold when the peak area ratio of the drug in the extracted DBS sample to the internal standard is less than 1.

Also provided herein are systems that include: a mass spectrometer configured to (i) generate a peak representing a drug (e.g., a cardiac drug, an anticoagulant, a bronchodilator, an antibiotic, an anti-epileptic, an antidepressant, an antimanic agent, an antipsychotic, an antiretroviral, or an immune modulator) in an extracted dried blood spot (DBS) sample from a subject (e.g., a pregnant subject) after a treatment for a disease has been administered and (ii) generate a peak representing an internal standard; a computer-readable memory including computer-executable instructions; and one or more processors communicatively coupled to the mass spectrometer and configured to execute the computer-executable instructions, wherein when the one or more processors are executing the computer-executable instructions, the one or more processors are configured to carry out operations including: determining a peak area ratio of the drug in the extracted DBS sample to the internal standard; and identifying the administered treatment as being effective when the peak area ratio of the drug in the extracted DBS sample to the internal standard is less than 1.

Also provided herein are systems that include: a mass spectrometer configured to (i) generate a peak representing a drug (e.g., cardiac drug, an anticoagulant, a bronchodilator, an antibiotic, an anti-epileptic, an antidepressant, an antimanic agent, an antipsychotic, an antiretroviral, or an immune modulator) in an extracted dried blood spot (DBS) sample from a subject (e.g., a pregnant subject) after a treatment for a disease has been administered, (ii) generate a peak representing a first internal standard, and (iii) generate a peak representing a second internal standard; a computer-readable memory including computer-executable instructions; and one or more processors communicatively coupled to the mass spectrometer and configured to execute the computer-executable instructions, wherein when the one or more processors are executing the computer-executable instructions, the one or more processors are configured to carry out operations including: determining a peak area ratio of the drug in the extracted DBS sample to the first internal standard; determining a peak area ratio of the drug in the extracted DBS sample to the second internal standard; and determining that an amount of the drug in the pregnant subject is within an acceptable range when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Also provided herein are systems that include: a mass spectrometer configured to (i) generate a peak representing a drug (e.g., cardiac drug, an anticoagulant, a bronchodilator, an antibiotic, an anti-epileptic, an antidepressant, an antimanic agent, an antipsychotic, an antiretroviral, or an immune modulator) in an extracted dried blood spot (DBS) sample from a subject (e.g., a pregnant subject) after a treatment for a disease has been administered, (ii) generate a peak representing a first internal standard, and (iii) generate a peak representing a second internal standard; a computer-readable memory including computer-executable instructions; and one or more processors communicatively coupled to the mass spectrometer and configured to execute the computer-executable instructions, wherein when the one or more processors are executing the computer-executable instructions, the one or more processors are configured to carry out operations including: determining a peak area ratio of the drug in the extracted DBS sample to the first internal standard; determining a peak area ratio of the drug in the extracted DBS sample to the second internal standard; and identifying the administered treatment as being effective when: (i) the peak area ratio of the drug in the extracted DBS sample to the first internal standard is greater than 1 and (ii) the peak area ratio of the drug in the extracted DBS sample to the second internal standard is less than 1, wherein the peak area ratio of the drug in the extracted DBS sample to the first internal standard relates to a minimal therapeutic efficacy level and the peak area ratio of the drug in the extracted DBS sample to the second internal standard relates to a maximal therapeutic efficacy level.

Dried Blood Spot (DBS) Cards

Provided herein are dried blood spot (DBS) cards that include a filter paper, a pre-stained region including at least one internal standard of a drug (e.g., stable-labeled [$^{13}C_2$, $^2H_3$]-teriflunomide (internal standard, ISTD), or [$^2H_6$]-Teriflunomide), wherein the at least one internal standard of the drug is deposited at a threshold level onto the pre-stained region.

In some examples, the drug is a drug for the treatment of relapse-remitting multiple sclerosis (e.g., teriflunomide)

In some examples of any of the DBS cards described herein, the at least one internal standard comprises a first internal standard (e.g., a minimum effective concentration) and a second internal standard (e.g., a minimum toxic concentration or a maximum therapeutic concentration).

In some examples of any of the DBS cards described herein, the DBS card includes three or more pre-stained regions including the at least one internal standard of the drug.

In some examples of any of the DBS cards described herein, the DBS card further includes a patient identifying information (e.g., a barcode).

Kits

The development of a kit allowing the direct comparison of teriflunomide/ISTD ratio in an unknown sample facilitates the analytical phase and is amenable to any lab equipped with an LC-MS/MS system. Provided herein are kits that consist essentially of or consist of at least a single DBS card (e.g., any of the DBS cards described herein) that include an internal standard (e.g., a single internal standard or at least two internal standards), a single-use lancet (e.g., a single-use finger pricking tool), a syringe with a needle, a container (e.g., a gas-impermeable sealable bag (e.g., a foil bag)) with a desiccant packet, an alcohol swab, a sterile gauze swab, a patient form, technical instructions for how to collect a blood sample, and an envelope (e.g., a stamped envelope). In some examples, the internal standards are labeled, e.g., with a radioisotope, a fluorophore, or a quencher.

OTHER EMBODIMENTS

While certain embodiments have been described, other embodiments are possible. For example, while some of the above processes have been described with respect to teriflunomide, it should be understood that the processes can be used to detect the levels of other substances. For example, the process can be used to detect the levels of other medications used to treat multiple sclerosis, such as fingolimod, cladribine, siponimod, and dimethyl fumarate. Similarly, the processes can be used to detect the levels of other medications with long in vivo half-lives, which might be problematic for pregnant subjects. Examples of such drugs include antiarrhythmic drugs (e.g., digoxin), anticoagulants (e.g., warfarin), anti-epileptics (e.g., carbamazepine, felbamate, lamotrigine, phenobarbital), antidepressants, antimanics or antipsychotics (e.g., citalopram, clomipramine, fluoxetine, lithium, nortriptyline, olanzapine, sertraline), antiretrovirals (e.g., nevirapine), immune modulators (e.g., hydroxychloroquine, sirolimus, glucocorticoids).

The processes described herein can be used for any drug and/or any medications where it is beneficial to maintain the plasma concentration level of the drug and/or medication within a certain concentration range, and/or that have a narrow therapeutic index. Examples of drugs that have a narrow therapeutic index include: cardiac drugs (e.g., digoxin, disopyramide, procainamide), anticoagulants (e.g., warfarin, low-molecular weight heparin, unfractionated heparin), bronchodilators (e.g., theophylline), antibiotics (e.g., amikacin, gentamicin, tobramycin, vancomycin, netilmicin), anti-epileptics (e.g., carbamazepine, felbamate, gabapentin, lamotrigine, levetiracetam, oxcarbazepine, phenobarbital, phenytoin, valproic acid, and vigabatrin), antidepressants/antimanics/antipsychotics (e.g., amitriptyline, bupropion, citalopram, clomipramine, clozapine, duloxetine, fluoxetine, haloperidol, imipramine, lithium, nortriptyline, olanzapine, paroxetine, quetiapine, risperidone, sertraline, venlafaxine), antiretrovirals (e.g., atazanavir, indinavir, nelfinavir, nevirapine, lopinavir, ritonavir, saquinavir), immune modulators (e.g., azathioprine, cyclosporine, hydroxychloroquine, sirolimus, tacrolimus, corticosteroids). Similarly, it should be understood that it may be beneficial for other reasons to maintain teriflunomide below a certain threshold level outside of pregnancy.

Likewise, while the above processes have been described following collection of a blood sample from a finger prick, other blood collection techniques can be used. For example, a blood sample can also be collected from a venous site, a palm of the hand prick, an arm prick, a calf prick, or a thigh prick. For subjects who have poor irrigation of distal extremities, venipuncture is an alternative that can be performed by the skilled medical practitioner (e.g., a neurologist, a doctor, or a nurse), and can be facilitated using a syringe of 1 mL. LC-MS/MS analysis can also be done using an automated direct elution or an online extraction system that works as a front end for a LC-MS/MS system. For the one or the other method, standard solutions of teriflunomide and ISTD are used to calibrate the MS/MS system. Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of monitoring treatment for multiple sclerosis in a pregnant subject, the method comprising:

(a) extracting a drug from a dried blood spot (DBS) sample to produce an extracted DBS sample, the DBS sample being from a pregnant subject after a treatment for multiple sclerosis to the pregnant subject has been administered, wherein the DBS sample comprises blood obtained from the pregnant subject and a filter paper pretreated with a first internal standard;

(b) performing mass spectrometry on the extracted DBS sample;

(c) determining a peak area ratio of the drug in the extracted DBS sample to the first internal standard; and (d) identifying the administered treatment as being below an internal standard threshold when the peak area ratio of the drug in the extracted DBS sample to the first internal standard is less than 1.

2. The method of claim 1, wherein the administered treatment is administration of a drug for relapse-remitting multiple sclerosis.

3. The method of claim 1, wherein the administered treatment and the drug are teriflunomide.

4. The method of claim 3, wherein the peak area ratio of the drug in the extracted DBS sample to the first internal standard being less than 1 indicates that a level of teriflunomide in the pregnant subject is non-toxic to a fetus of the pregnant subject.

5. The method of claim 3, wherein the peak area ratio of the drug in the extracted DBS sample to the first internal standard being greater than 1 indicates that a level of a teriflunomide in the pregnant subject is harmful to a fetus of the pregnant subject.

6. The method of claim 3, wherein the internal standard threshold is 0.02 mcg/mL of a teriflunomide.

7. The method of claim 6, wherein the teriflunomide is $[^{2}H_{6}]$-Teriflunomide or $[^{13}C_{2}, 2H_{3}]$-Teriflunomide.

8. The method of claim 1, wherein the DBS sample is a blood sample obtained from a finger prick, a venipuncture, an arm prick, a calf prick, a thigh prick, or a palm of hand prick.

9. The method of claim 1, wherein the peak area ratio of the drug in the extracted DBS sample to the first internal standard relates to a maximal therapeutic efficacy level.

10. The method of claim 1, wherein the filter paper is pretreated with a threshold amount of the first internal standard.

11. The method of claim 1, wherein the DBS sample comprises blood obtained from the pregnant subject and the filter paper pretreated with (i) the first internal standard and (ii) a second internal standard.

12. The method of claim 11, wherein the filter paper is pretreated with a threshold amount of the first internal standard and a threshold amount of the second internal standard.

13. The method of claim 11, further comprising determining a peak area ratio of the drug in the extracted DBS sample to the second internal standard.

14. The method of claim 13, wherein the peak area ratio of the drug in the extracted DBS sample to the second internal standard relates to a minimal therapeutic efficacy level.

15. The method of claim 14, further comprising determining that an amount of the drug in the pregnant subject is within an acceptable range when: (i) the peak area ratio of the drug in the extracted DBS sample to the first internal standard is less than 1 and (ii) the peak area ratio of the drug in the extracted DVS sample to the second internal standard is greater than 1.

16. The method of claim 15, wherein the first internal standard is $[^{2}H_{6}]$-Teriflunomide and the second internal standard is $[^{13}C_{2}, 2H_{3}]$-Teriflunomide.

17. The method of claim 15, wherein the first internal standard is $[^{13}C_{2}, 2H_{3}]$-Teriflunomide $[^{2}H_{6}]$-Teriflunomide and the second internal standard is $[^{2}H_{6}]$-Teriflunomide.

* * * * *